United States Patent
Kageyama et al.

(10) Patent No.: US 10,766,996 B2
(45) Date of Patent: Sep. 8, 2020

(54) METHOD FOR PRODUCING POLYTHIOL COMPOUND, METHOD FOR PRODUCING CURABLE COMPOSITION, AND METHOD FOR PRODUCING CURED PRODUCT

(71) Applicant: HOYA LENS THAILAND LTD., Thamyburi, Pathumthani (TH)

(72) Inventors: Yukio Kageyama, Tokyo (JP); Masahisa Kousaka, Tokyo (JP); Tomofumi Ohnishi, Tokyo (JP)

(73) Assignee: HOYA LENS THAILAND LTD., Pathumthani (TH)

( * ) Notice: Subject to any disclaimer, the term of this patent is extended or adjusted under 35 U.S.C. 154(b) by 25 days.

(21) Appl. No.: 16/015,670

(22) Filed: Jun. 22, 2018

(65) Prior Publication Data

US 2018/0362699 A1    Dec. 20, 2018

Related U.S. Application Data

(63) Continuation of application No. PCT/JP2017/028589, filed on Aug. 7, 2017.

(30) Foreign Application Priority Data

Aug. 5, 2016    (JP) .................. 2016-154957

(51) Int. Cl.
```
C08G 18/38     (2006.01)
C07C 321/14    (2006.01)
C07C 319/14    (2006.01)
C07C 319/22    (2006.01)
C08G 18/76     (2006.01)
G02B 1/04      (2006.01)
C07C 319/20    (2006.01)
```
(52) U.S. Cl.
CPC ........ *C08G 18/3876* (2013.01); *C07C 319/14* (2013.01); *C07C 319/22* (2013.01); *C07C 321/14* (2013.01); *C08G 18/7642* (2013.01); *G02B 1/041* (2013.01)

(58) Field of Classification Search
CPC ................................. C08G 18/38

USPC ......................................... 528/373
See application file for complete search history.

(56) References Cited

U.S. PATENT DOCUMENTS

2015/0018507 A1    1/2015    Jang et al.

FOREIGN PATENT DOCUMENTS

| | | |
|---|---|---|
| CN | 104066716 A | 9/2014 |
| CN | 104321306 A | 1/2015 |
| JP | H02-270859 A | 11/1990 |
| JP | 2015-506947 A | 3/2015 |
| WO | 2015/137402 A1 | 9/2015 |

OTHER PUBLICATIONS

Jul. 29, 2019 Office Action issued in Chinese Patent Application No. 201780005125.5.
Oct. 24, 2017 International Search Report issued in International Patent Application PCT/JP2017/028589.
Mar. 26, 2019 Office Action issued in Japanese Patent Application No. 2016-154957.
May 31, 2019 extended Search Report issued in European Patent Application No. 17837124.1.
Feb. 5, 2019 International Preliminary Report on Patentability issued in International Patent Application PCT/JP2017/028589.
Apr. 26, 2020 Office Action issued in Chinese Patent Application No. 201780005125.5.

*Primary Examiner* — Duc Truong
(74) *Attorney, Agent, or Firm* — Oliff PLC

(57) ABSTRACT

Provided is a method for producing a polythiol compound, including reacting 2-mercaptoethanol with an epihalohydrin, wherein the reaction is carried out in the presence of a halide selected from the group consisting of a 2,3-dihalogeno-1-propanol and an allyl halide, and an amount of the halide in the reaction is more than 0.50% by mass and 10.00% by mass or less with respect to the total amount of the halide and the epihalohydrin. Also provided are a method for producing a curable composition, including producing a polythiol compound by the abovementioned production method, and a method for producing a cured product, including producing a curable composition by the abovementioned production method.

5 Claims, No Drawings

METHOD FOR PRODUCING POLYTHIOL COMPOUND, METHOD FOR PRODUCING CURABLE COMPOSITION, AND METHOD FOR PRODUCING CURED PRODUCT

CROSS-REFERENCE OF RELATED APPLICATIONS

This application is a Continuation of PCT International Application No. PCT/JP2017/028589 filed on Aug. 7, 2017, which was published under PCT Article 21(2) in Japanese and claims priority under 35 U.S.C § 119(a) to Japanese Patent Application No. 2016-154957 filed on Aug. 5, 2016. The above applications are hereby expressly incorporated by reference, in their entirety, into the present application.

TECHNICAL FIELD

One aspect of the present disclosure relates to a method for producing a polythiol compound, a method for producing a curable composition, and a method for producing a cured product.

BACKGROUND ART

Polythiol compounds have been used as synthetic raw materials for obtaining various resins (see Japanese Translation of PCT Application No. 2015-506947 (the entire disclosure of which is hereby specifically incorporated by reference)). For example, a polythiourethane resin can be synthesized by a curing reaction of a polythiol compound and a polyiso(thio)cyanate compound. The polythiourethane resin thus obtained is useful as a material for various optical components such as spectacle lenses.

SUMMARY

In the course of research aimed at additional enhancement of utility of polythiourethane resins, the inventors of the present disclosure focused attention on a tensile strength. Where a polythiourethane resin is inferior in tensile strength, fissures and cracks are likely to occur due to failure to withstand forces applied when processing optical components such as spectacle lenses. Meanwhile, where a polythiourethane resin having a high tensile strength is used, occurrence of fissures and cracks during processing of optical components can be prevented or reduced.

Further, one of the physical properties desired for polythiourethane resins is high heat resistance. This is so because during processing of an optical component, in many cases, heat treatment is carried out when forming a functional film or the like, and it is therefore desirable that a polythiourethane resin used as the base material of the optical component have heat resistance capable of withstanding such heat treatment.

However, the investigation conducted by the inventors of the present disclosure has indicated that it is not easy to improve the tensile strength of a polythiourethane resin without causing a large decrease in heat resistance.

According to one aspect of the present disclosure, there is provided means for improving the tensile strength without causing a large decrease in heat resistance of a polythiourethane resin obtained by a curing reaction of a polythiol compound and a polyiso(thio)cyanate compound.

One aspect of the present disclosure relates to:

a method for producing a polythiol compound, including reacting 2-mercaptoethanol with an epihalohydrin, wherein the reaction is carried out in the presence of a halide selected from the group consisting of a 2,3-dihalogeno-1-propanol and an allyl halide, and an amount of the halide in the reaction is more than 0.50% by mass and 10.00% by mass or less with respect to the total amount of the halide and the epihalohydrin.

In the course of subsequent intensive research, the inventors of the present disclosure focused attention on the production process of a polythiol compound which is a raw material for synthesizing a polythiourethane resin. As a result of additional intensive research, it has been found that in the production of a polythiol compound, a step of reacting 2-mercaptoethanol with an epihalohydrin needs to be carried out in the presence of a halide selected from the group consisting of a 2,3-dihalogeno-1-propanol and an allyl halide, the amount thereof being more than 0.50% by mass and 10.00% by mass or less with respect to the total amount of the halide and the epihalohydrin. The halide is partly included in impurities which are supposed to be in a total amount of 0.5% by mass or less in the aforementioned Japanese Translation of PCT Application No. 2015-506947. A surprising new finding of the intensive research conducted by the inventors of the present disclosure is that where the abovementioned step is carried out in the presence of a component, which is required to be excluded in the Japanese Translation of PCT Application No. 2015-506947, in the abovementioned amount with respect to the epihalohydrin, the tensile strength of a polythiourethane resin can be improved without causing a large decrease in heat resistance.

A method for producing a polythiol compound according to one aspect of the present disclosure has thus been completed.

According to one aspect of the present disclosure, the tensile strength of a cured product (polythiourethane resin) obtained by a curing reaction of a polythiol compound and a polyiso(thio)cyanate compound can be improved without causing a large decrease in heat resistance.

DESCRIPTION OF EMBODIMENTS

[Method for Producing Polythiol Compound]

Hereinafter, a method for producing a polythiol compound according to one aspect of the present disclosure will be described in greater detail. The heat resistance and tensile strength described hereinbelow are assumed to be the heat resistance and tensile strength of a cured product (polythiourethane resin) obtained by a curing reaction of a polythiol compound and a polyiso(thio)cyanate compound.

The polythiol compound can be synthesized through a step of reacting 2-mercaptoethanol:

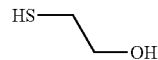

and an epihalohydrin:

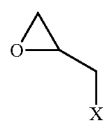

X in the epihalohydrin represents a halogen atom. The halogen atom is a fluorine atom, a chlorine atom, a bromine atom, an iodine atom or the like, may be a chlorine atom and a bromine atom, or may be a chlorine atom (that is, epichlorohydrin).

In the method for producing a polythiol compound according to one aspect of the present disclosure, the abovementioned step is carried out in the presence of a halide selected from the group consisting of a 2,3-dihalogeno-1-propanol and an allyl halide, the amount thereof being more than 0.50% by mass and 10.00% by mass or less with respect to the total amount with the epihalohydrin. As a result, it is possible to improve the tensile strength without causing a large decrease in heat resistance of the polythiourethane resin obtained by using the polythiol compound which is to be produced.

The halide present in the abovementioned step may be only one halide or two or more halides. When the abovementioned step is carried out in the presence of two or more halides, the amount of the halide means the total amount of these two or more halides. Thus, in the present disclosure and the present description, unless otherwise specified, components that can take different structures may be used singly or in combination of two or more thereof. When two or more components are used, the content means the total content of the two or more components. From the viewpoint of further improving the tensile strength, the amount of the halide may be 0.60% by mass or more, or may be 0.70% by mass or more. From the viewpoint of improving the tensile strength while further suppressing the decrease in heat resistance, the amount of the halide may be 9.00% by mass or less, may be 8.00% by mass or less, may be 7.00% by mass or less, may be 6.00% by mass or less, may be 5.00% by mass or less, or may be 4.00% by mass or less, may be 3.00% by mass or less, may be 2.00% by mass or less, or may be 1.50% by mass or less.

The halogen atom contained in the 2,3-dihalogeno-1-propanol is, for example, a fluorine atom, a chlorine atom, a bromine atom, an iodine atom or the like, and may be a chlorine atom or a bromine atom. In addition, the two halogen atoms contained in the 2,3-dihalogeno-1-propanol may be the same or different. Specific examples of the 2,3-dihalogeno-1-propanol include 2,3-dichloro-1-propanol, 2,3-dibromo-1-propanol and the like.

The halogen atom contained in the allyl halide is, for example, a fluorine atom, a chlorine atom, a bromine atom, an iodine atom and the like, may be a chlorine atom and a bromine atom, or may be a chlorine atom. That is, the allyl halide may be allyl chloride.

One aspect of the polythiol compound obtained through the abovementioned step is one or more polythiol compounds selected from the group consisting of a polythiol compound represented by the following Formula (3) (4,8-bismercaptomethyl-3,6,9-trithiaundecane-1,11-diol), a polythiol compound represented by the following Formula (4) (4,7-bismercaptomethyl-3,6,9-trithiaundecane-1,11-diol), and a polythiol compound represented by the following Formula (5) (5,7-bismercaptomethyl-3,6,9-trithiaundecane-1,11-diol). These three polythiol compounds are usually obtained as a mixture of these three isomers.

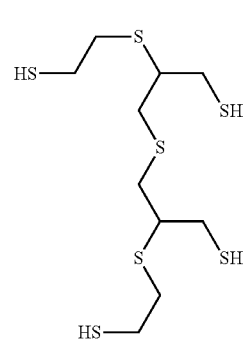

Formula (3)

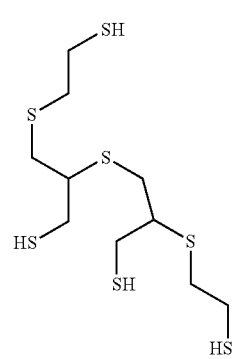

Formula (4)

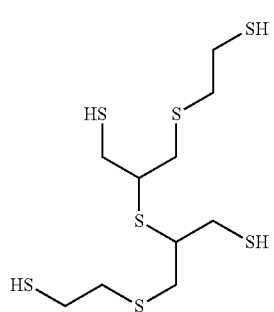

Formula (5)

In addition, one aspect of the polythiol compound obtained through the abovementioned step is a polythiol compound represented by the following Formula (7).

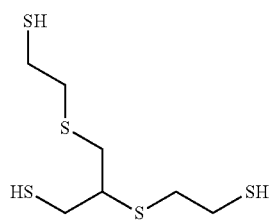

Formula (7)

Hereinafter, in the method for producing a polythiol compound according to one aspect of the present disclosure, an aspect in which one or more polythiol compounds selected from the group consisting of the polythiol compound represented by Formula (3), the polythiol compound represented by Formula (4) and the polythiol compound represented by Formula (5) are obtained will be referred to as "Aspect A", and an aspect in which the polythiol compound represented by Formula (7) is obtained will be referred to as "Aspect B". In each of Aspect A and Aspect B, the step of reacting 2-mercaptoethanol with an epihalohydrin is carried out in the presence of a halide selected from the group consisting of a 2,3-dihalogeno-1-propanol and an allyl halide, the amount of the halide being more than 0.50% by mass and 10.00% by mass or less with respect to the total amount with the epihalohydrin.

Hereinafter, Aspect A and Aspect B will be described in greater detail.

<Aspect A>

Aspect A includes:

a Step 1A of reacting 2-mercaptoethanol with an epihalohydrin;

a Step 2A of reacting a polyol compound which has been obtained in Step 1A and is represented by Formula (1):

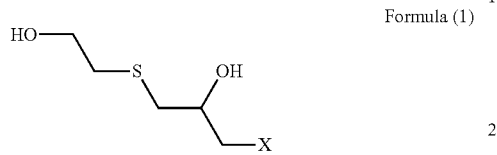

Formula (1)

[in Formula (1), X represents a halogen atom]

with an alkali metal sulfide to obtain a polyol compound represented by Formula (2):

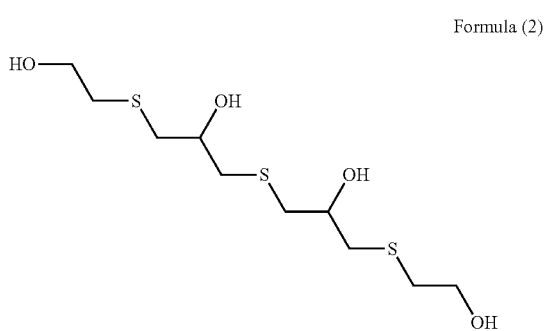

Formula (2)

a Step 3A of reacting the polyol compound represented by Formula (2) with thiourea in the presence of an acid to obtain an isothiuronium salt;

a Step 4A of hydrolyzing the isothiuronium salt in the presence of a base to obtain a polythiol salt; and a Step 5A of converting the polythiol salt into a polythiol with an acid to obtain one or more polythiol compounds selected from the group consisting of the polythiol compound represented by Formula (5), the polythiol compound represented by Formula (6), and the polythiol compound represented by Formula (7).

Steps 1A to 5A will be sequentially described hereinbelow.

(Step 1A)

In Step 1A, a polyol compound represented by the following Formula (1) can be obtained by reacting 2-mercaptoethanol with an epihalohydrin.

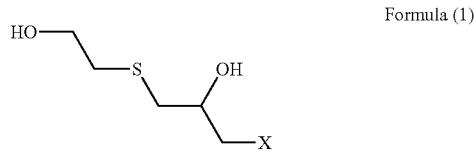

Formula (1)

That is, in Step 1A, the polyol compound represented by Formula (1) can be obtained according to the following Reaction Scheme Example 1.

Reaction Scheme Example 1

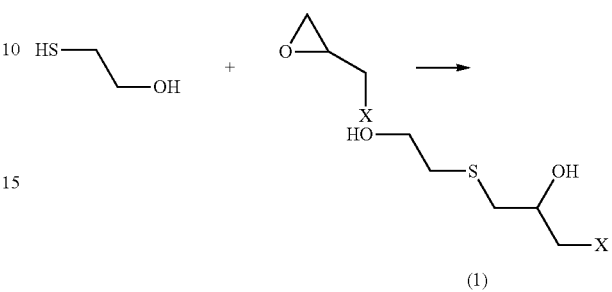

(1)

In the epihalohydrin and in Formula (1), X represents a halogen atom. For example, by using epichlorohydrin (X=chlorine atom) as the epihalohydrin in Step 1A, a polyol compound in which X in Formula (1) is a chlorine atom can be obtained. Further, by using epibromohydrin (X=bromine atom) as the epihalohydrin in Step 1A, a polyol compound in which X in Formula (1) is a bromine atom can be obtained. The details relating to the halogen atom contained in the epihalohydrin are as described hereinabove. The same applies to the halogen atom represented by X included in Formula (1). In Aspect A, Step 1A is carried out in the presence of a halide selected from the group consisting of a 2,3-dihalogeno-1-propanol and an allyl halide, the amount of the halide being more than 0.50% by mass and 10.00% by mass or less with respect to the total amount with the epihalohydrin. Details relating to the amount of the halide in Step 1A are as described hereinabove.

The reaction of 2-mercaptoethanol and an epihalohydrin in Step 1A may be carried out in the presence of a catalyst. As the catalyst, various known catalysts can be used, and it is possible to use a tertiary amine. Tertiary alkyl amines may be as tertiary amines. Specific examples of tertiary amines include trimethylamine, triethylamine, tripropylamine, tributylamine, N,N-dimethylcyclohexylamine, N,N-dicyclohexylmethylamine, and the like. Specific examples of tertiary amines may include triethylamine, tripropylamine, and tributylamine. Specific examples of tertiary amines may include triethylamine and tributylamine.

The reaction temperature in Step 1A and the reaction temperature in Step 2A described hereinbelow can be, for example, about 0° C. to 60° C. The reaction time in Step 1A can be, for example, about 0.5 h to 10 h. In the present disclosure and the present description, the "reaction temperature" is the liquid temperature of a reaction solution and is also referred to as "internal temperature".

In one aspect, Step 1A can be carried out, for example, in the following manner. First, 2-mercaptoethanol may be mixed with a catalyst to obtain a mixed solution. It is possible to mix a tertiary amine as the catalyst. If necessary, a solvent (for example, an alcohol) may be added. Then, the halide and the epihalohydrin are added to the mixed solution simultaneously or sequentially. It is possible that the halide be mixed with the epihalohydrin and then added to the mixture. The halide and the epihalohydrin may be added dropwise to the mixed solution, for example, after mixing. The dropping time can be, for example, about 0.1 h to 5 h, but is not particularly limited. During the dropwise addition, the mixed solution may be stirred as necessary. The epihalohydrin can be reacted with 2-mercaptoethanol by using the epihalohydrin at a ratio in a range of, for example, 0.5 mol to 3.0 mol, 0.7 mol to 2.0 mol, or 0.9 mol to 1.1 mol with respect to 1.0 mol of 2-mercaptoethanol. The tertiary amine can be used in an amount of, for example, about 0.005 mol to 0.1 mol, with respect to 1.0 mol of the epihalohydrin. After the addition of the halide and the epihalohydrin, the mixed solution may be aged for about 0.5 h to 10 h as necessary. During aging, the mixture may be left to stand or may be stirred.

(Step 2A)

Step 2A is a step of reacting the polyol compound obtained in Step 1A and represented by Formula (1) with an alkali metal sulfide to obtain a polyol compound represented by Formula (2).

Formula (2)

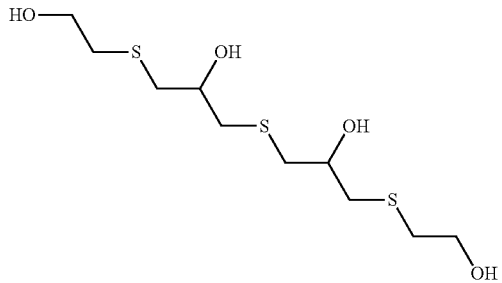

For example, taking, as an example, the case of using sodium sulfide as an alkali metal sulfide, in Step 2A, the polyol compound represented by Formula (2) can be obtained according to the following Reaction Scheme Example 2. The numerical values described in the following reaction scheme examples are on a molar basis.

Reaction Scheme Example 2

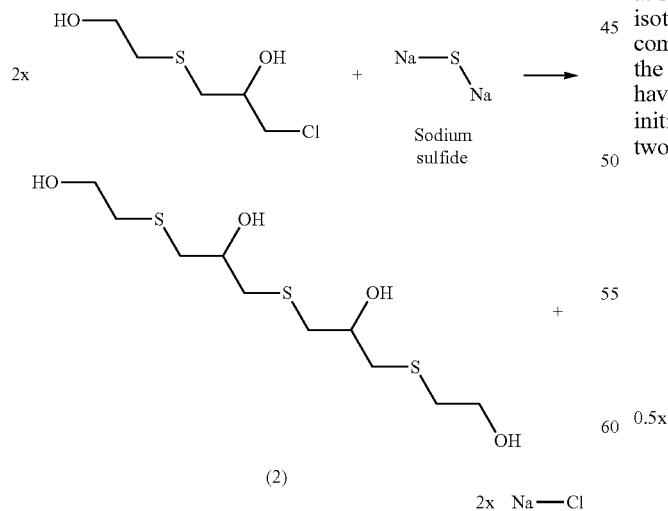

After the reaction of Step 1A, the reaction solution including the target substance obtained by the reaction may be used as it is in Step 2A, but the reaction solution after the reaction in Step 1A may be also purified by a known method to isolate the target substance or increase the concentration thereof and then used in the next step. Alternatively, the reaction solution after the reaction in Step 1A can be diluted with a solvent (for example, toluene and the like) and then used in the next step. The above considerations are also applicable to stages after various below-described reactions.

The abovementioned Reaction Scheme Example 2 relates to an example in which the alkali metal atom contained in the alkali metal sulfide is a sodium atom. However, the alkali metal atom contained in the alkali metal sulfide may be another alkali metal atom such as a lithium atom and a potassium atom. The alkali metal sulfide can be reacted with the polyol compound represented by Formula (1) at a ratio within a range of, for example, 0.2 mol to 2.0 mol, 0.3 mol to 1.2 mol, or 0.4 mol to 0.6 mol with respect to 1.0 mol of the polyol compound represented by Formula (1). The alkali metal sulfide may be in the form of a hydrate. The amount relating to a hydrate is assumed to mean the amount including water of hydration. The alkali metal sulfide may be used as it is for the reaction of Step 2A or may be used in the form of a solution such as an aqueous solution. In one aspect, the solution of the alkali metal sulfide can be added dropwise to a reaction solution including the polyol compound represented by Formula (1). The dropping time can be, for example, about 0.1 h to 5 h, but is not particularly limited. During the dropwise addition, the reaction solution may be stirred as necessary. Such a reaction solution may be aged for about 0.5 h to 10 h as necessary after the addition of the alkali metal sulfide. During aging, the reaction solution may be left to stand or may be stirred.

(Step 3A)

Step 3A is a step of reacting the polyol compound obtained in Step 2A and represented by Formula (2) with thiourea in the presence of an acid to obtain an isothiuronium salt. The "isothiuronium salt" is a quaternary salt of isothiourea. Taking, as an example, the case of using hydrochloric acid as an acid, for example, when a polyol compound represented by Formula (2) is reacted with thiourea in the presence of an acid, the isothiuronium salt shown in the following Reaction Scheme Example 3 can be obtained. In Reaction Scheme Example 3, the isothiuronium salt having the skeleton of the polythiol compound (3) is shown, but in this reaction, it is possible to obtain an isothiuronium salt of at least one kind selected from the group consisting of the isothiuronium salt having the skeleton of the polythiol compound (3), the isothiuronium salt having the skeleton of the polythiol compound (4), and the isothiuronium salt having the skeleton of the polythiol compound (5), and by initiating a rearrangement reaction, it is possible to obtain two or three among the abovementioned isothiuronium salts.

Reaction Scheme Example 3

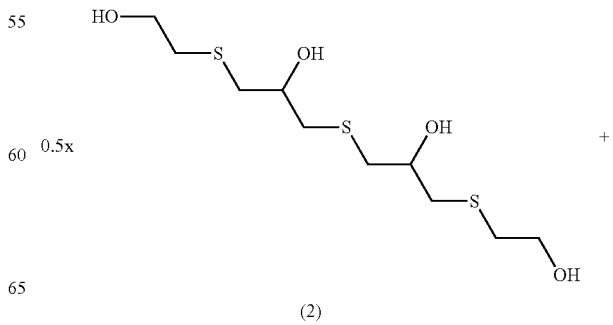

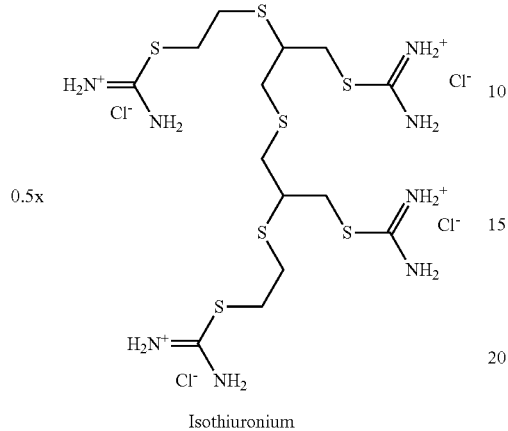

Thiourea

Isothiuronium

In the Reaction Scheme Example 3, an example is shown in which hydrogen chloride (HCl) is used as an acid, but the acid used in Step 3A is not limited to hydrogen chloride, and various inorganic acids and organic acids can be used. Examples of the inorganic acids include hydrogen chloride, sulfuric acid and the like, and examples of organic acids include formic acid and the like. The form of addition of an acid is not limited, and the acid can be added, for example, as an aqueous solution. The concentration of the acid in the aqueous solution is not particularly limited, and can be, for example, about 10% by mass to 80% by mass. In Step 3A, the acid can be used at a ratio of, for example, 2.0 mol to 12.0 mol, or 3.0 mol to 8.0 mol, and thiourea can be used at a ratio of, for example, 3.0 mol to 6.0 mole, or 4.5 mol to 5.5 mol with respect to 1.0 mol of the polyol compound represented by Formula (2). The reaction temperature in Step 3A can be, for example, from 40° C. to the reflux temperature, or from about 90° C. to 120° C., and the reaction time can be, for example, about 1 h to 24 h.

(Step 4A)

Step 4A is a step of hydrolyzing the isothiuronium salt obtained in Step 3A in the presence of a base to obtain a polythiol salt. The polythiol salt obtained herein has a structure in which a hydrogen atom of one or more thiol groups among four thiol groups (—SH) present in one molecule in the structure of the polythiol compound represented by Formula (3), Formula (4) or Formula (5) is substituted. In Step 4A, it is also possible to obtain two or more polythiol salts having different structures. The polythiol salt may be an alkali metal salt of polythiol or an ammonium salt of polythiol. The type of salt can be adjusted by the type of base used for hydrolysis. As an example, a mode of obtaining an alkali metal salt as a polythiol salt will be described hereinbelow.

The alkali metal salt of polythiol has a structure in which an alkali metal salt of a thiol group (—SM; M represents an alkali metal atom) is introduced in the molecular terminal as a result of hydrolysis of the isothiuronium salt obtained in Step 3A. For example, by hydrolyzing the isothiuronium salt having the skeleton of the polythiol compound represented by Formula (3) by using sodium hydroxide as a base, it is possible to obtain the alkali metal salt (sodium salt) of the polythiol shown in the following Reaction Scheme Example 4.

Reaction Scheme Example 4

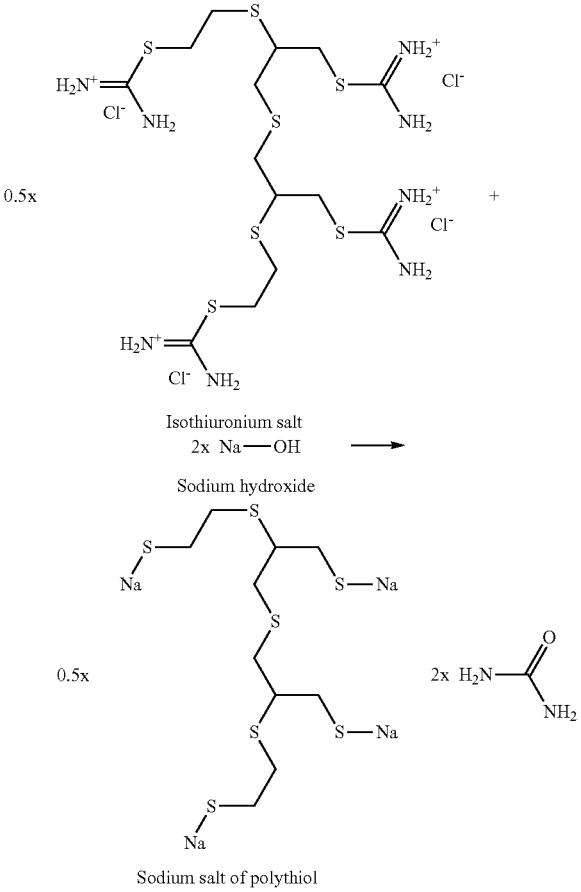

Sodium salt of polythiol

In the Reaction Scheme Example 4, an example is shown in which sodium hydroxide is used as the base. However, the base used in Step 4A is not limited to sodium hydroxide, and various inorganic bases and organic bases can be used. The base may be an inorganic base. Examples of the inorganic base include sodium hydroxide, potassium hydroxide, ammonia and the like. The form of base addition is not limited, but it is possible to add the base as an aqueous solution. By adding the base as an aqueous solution, it is possible to hydrolyze the isothiuronium salt with water contained in the aqueous solution in the presence of the base. The base concentration in the aqueous solution is not particularly limited, and can be, for example, about 10% by mass to 60% by mass. The base can be used at a ratio of, for example, 1.0 mol to 4.0 mol, 1.0 mol to 3.0 mol, or 1.2 mol to 2.0 mol with respect to 1.0 mol of the acid used in Step 3A. An organic solvent can be added to the reaction solution including the isothiuronium salt after the reaction in Step 3A. The organic solvent can be arbitrarily added at any stage after the reaction in Step 3A. The amount of the organic solvent to be added can be, for example, about 0.2 times to 3.0 times, on the volume basis, that of the reaction solution after the reaction in Step 3A. As the organic solvent, for example, toluene, xylene, benzene and the like can be mentioned. The organic solvent may be toluene. In Step 4A, the reaction temperature can be, for example, about 10° C. to 80° C., and the reaction time can be, for example, about 1 h to 10 h.

(Step 5A)

Step 5A is a step of converting the polythiol salt obtained in Step 4A into a polythiol with an acid. As a result, it is possible to obtain one or more polythiol compounds selected from the group consisting of the polythiol compound represented by Formula (3), the polythiol compound represented by Formula (4) and the polythiol compound represented by Formula (5). For example, Reaction Scheme Example 5 for converting the polythiol sodium salt shown in Reaction Scheme Example 4 to polythiol by using hydrogen chloride (HCl) as an acid to obtain the polythiol compound represented by Formula (3) is shown below.

Reaction Scheme Example 5

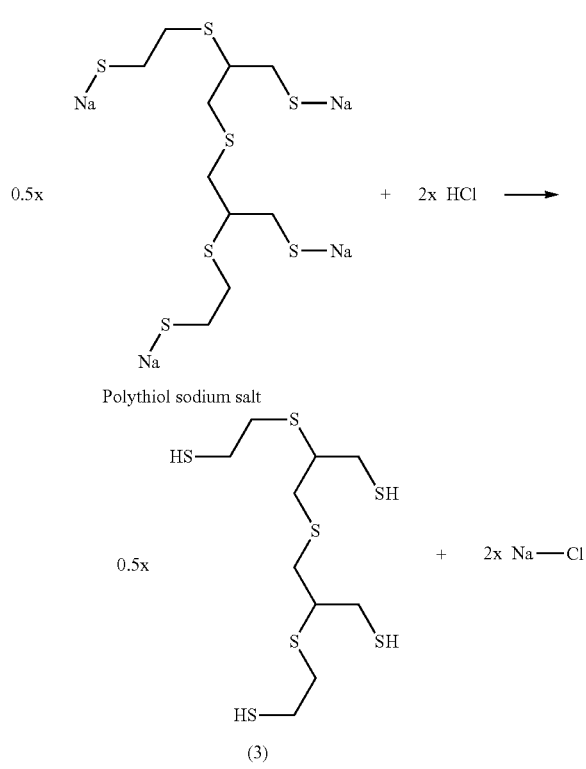

In the above Reaction Scheme Example 5, an example is shown in which hydrogen chloride is used as the acid. However, the acid to be used in Step 5A is not limited to hydrogen chloride, and various inorganic acids and organic acids can be used. The details relating to the acid to be used in Step 5A are as described in relation to the acid in Step 3A. The conversion to polythiol with the acid in Step 5A can be carried out using the acid in the form of an aqueous solution, for example, by acid washing. It is possible to carry out water washing after acid washing, for example, to carry out acid washing two or more times and to wash with water between acid washing cycles. The temperature of the environment in which Step 5A is performed is not particularly limited. Step 5A can be performed in an environment with a temperature of, for example, of 10° C. to 60° C., or 20° C. to 45° C. When an organic solvent is used in any of the steps, a step of distilling off the organic solvent from the reaction solution after Step 5A may be carried out by a known method. Further, subsequent steps such as filtration and distillation can also be carried out by known methods.

Each of the above steps can be performed in the atmospheric air and also can be performed in an atmosphere other than the atmospheric air, for example, under a nitrogen atmosphere. This also applies to each step in Aspect B described below.

With the above-described steps, it is possible to obtain one of the polythiol compound represented by Formula (3), the polythiol compound represented by Formula (4) and the polythiol compound represented by Formula (5), or a mixture of two or three thereof. When the polythiol compounds are obtained as a mixture of two or more thereof, each polythiol compound may be isolated by a known isolation method or may be used in a mixture as a synthetic raw material for obtaining various resins.

<Aspect B>

Aspect B includes:

a Step 1B of reacting 2-mercaptoethanol with an epihalohydrin to obtain a polyol compound represented by Formula (6);

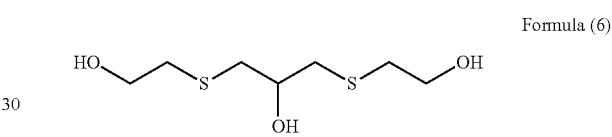

a Step 2B of reacting the polyol compound which is represented by Formula (6) with thiourea in the presence of an acid to obtain an isothiuronium salt;

a Step 3B of hydrolyzing the isothiuronium salt in the presence of a base to obtain a polythiol salt; and a Step 4B of converting the polythiol salt into a polythiol with an acid to obtain a polythiol compound represented by Formula (7).

Steps 1B to 4B will be sequentially described hereinbelow.

(Step 1B)

In Step 1B, a polyol compound represented by the following Formula (6) can be obtained by reacting 2-mercaptoethanol with an epihalohydrin.

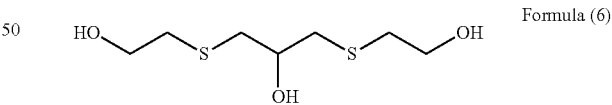

Details relating to the halogen atom contained in the epihalohydrin used in Step 1B are as described hereinabove. In Aspect B, Step 1B is carried out in the presence of a halide selected from the group consisting of a 2,3-dihalogeno-1-propanol and an allyl halide, the amount of the halide being more than 0.50% by mass and 10.00% by mass or less with respect to the total amount with the epihalohydrin. Details relating to the halide amount in Step 1B are also as described hereinabove.

Step 1B can be carried out in the presence of a base. For example, in Step 1B, the polyol compound represented by Formula (6) can be obtained according to the following Reaction Scheme Example 6.

Reaction Scheme Example 6

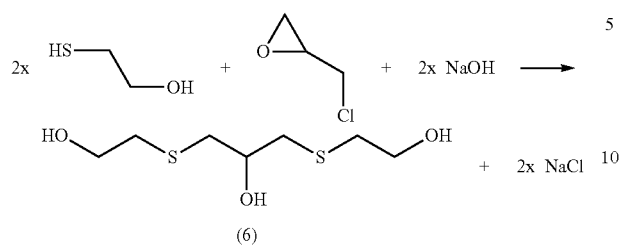

(6)

In the Reaction Scheme Example 6, an example is shown in which sodium hydroxide is used as the base. However, the base used in Step 1B is not limited to sodium hydroxide, and various inorganic bases and organic bases can be used. The base may be an inorganic base. Examples of the inorganic base include sodium hydroxide, potassium hydroxide, ammonia and the like.

The reaction temperature in Step 1B can be, for example, about 0° C. to 60° C. The reaction time in Step 1B can be, for example, about 0.5 h to 10 h. In one aspect, Step 1B can be performed, for example, in the following manner. First, 2-mercaptoethanol may be mixed with a base to obtain a mixed solution. A solvent (such as an alcohol) may be added as required. Thereafter, the halide and the epihalohydrin are added to the mixed solution simultaneously or sequentially. It is possible that the halide be mixed with the epihalohydrin and then added to the mixture. The halide and the epihalohydrin may be added dropwise to the mixed solution, for example, after mixing. The dropping time can be, for example, about 0.1 h to 5 h, but is not particularly limited. During the dropwise addition, the mixed solution may be stirred as necessary. The epihalohydrin can be reacted with 2-mercaptoethanol by using the epihalohydrin at a ratio in a range of, for example, 0.5 mol to 3.0 mol, 0.7 mol to 2.0 mol, or 0.9 mol to 1.1 mol with respect to 2.0 mol of 2-mercaptoethanol. The base can be used at a ratio within a range of, for example, about 0.5 mol to 3.0 mol, 0.7 mol to 2.0 mol, or 0.9 mol to 1.1 mol with respect to 1.0 mol of 2-mercaptoethanol. After the addition of the halide and the epihalohydrin, the mixed solution may be aged for about 0.5 h to 10 h as necessary. During aging, the mixture may be left to stand or may be stirred.

(Step 2B)

Step 2B is a step of reacting the polyol compound obtained in Step 2A and represented by Formula (6) with thiourea in the presence of an acid to obtain an isothiuronium salt. Taking, as an example, the case of using hydrochloric acid as an acid, for example, when a polyol compound represented by Formula (6) is reacted with thiourea in the presence of an acid, the isothiuronium salt having the skeleton of a polythiol compound (7) shown in the following Reaction Scheme Example 7 can be obtained.

Reaction Scheme Example 7

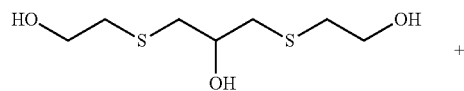

+

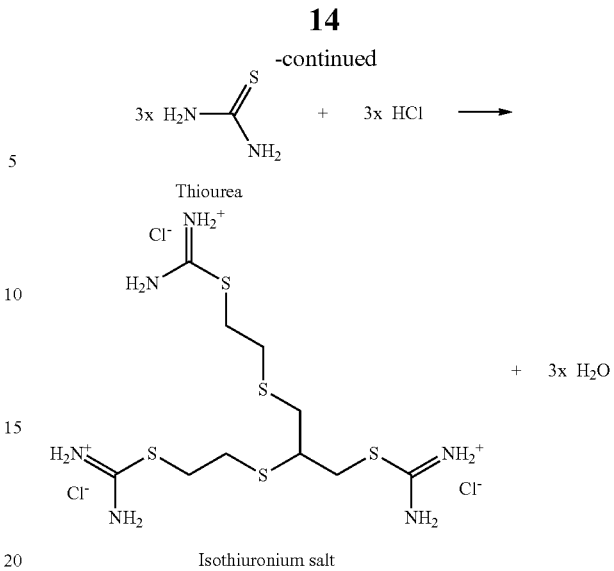

In the Reaction Scheme Example 7, an example is shown in which hydrogen chloride (HCl) is used as an acid. However, the acid used in Step 2B is not limited to hydrogen chloride, and various inorganic acids and organic acids can be used. Examples of the inorganic acids include hydrogen chloride, sulfuric acid and the like, and examples of organic acids include formic acid and the like. The form of addition of an acid is not limited, and the acid can be added, for example, as an aqueous solution. The concentration of the acid in the aqueous solution is not particularly limited, and can be, for example, about 10% by mass to 80% by mass. In Step 2B, the acid can be used at a ratio of, for example, 2.0 mol to 12.0 mol, or 3.0 mol to 8.0 mol, and thiourea can be used at a ratio of, for example, 2.0 mol to 5.0 mol, or 3.5 mol to 4.5 mol with respect to 1.0 mol of the polyol compound represented by Formula (6). The reaction temperature in Step 2B can be, for example, from 40° C. to the reflux temperature, or from about 90° C. to 120° C., and the reaction time can be, for example, about 1 h to 24 h.

(Step 3B)

Step 3B is a step of hydrolyzing the isothiuronium salt obtained in Step 2B in the presence of a base to obtain a polythiol salt. The polythiol salt obtained herein has a structure in which a hydrogen atom of one or more thiol groups among three thiol groups (—SH) present in one molecule in the structure of the polythiol compound represented by Formula (7) is substituted. In Step 3B, it is also possible to obtain two or more polythiol salts having different structures. The polythiol salt may be an alkali metal salt of polythiol or an ammonium salt of polythiol. The type of salt can be adjusted by the type of base used for hydrolysis. As an example, a mode of obtaining an alkali metal salt as a polythiol salt will be described hereinbelow.

The alkali metal salt of polythiol has a structure in which an alkali metal salt of a thiol group (—SM; M represents an alkali metal atom) is introduced in the molecular terminal as a result of hydrolysis of the isothiuronium salt obtained in Step 2B. For example, by hydrolyzing the isothiuronium salt having the skeleton of the polythiol compound represented by Formula (7) by using sodium hydroxide as a base, it is possible to obtain the alkali metal salt (sodium salt) of the polythiol shown in the following Reaction Scheme Example 8.

Reaction Scheme Example 8

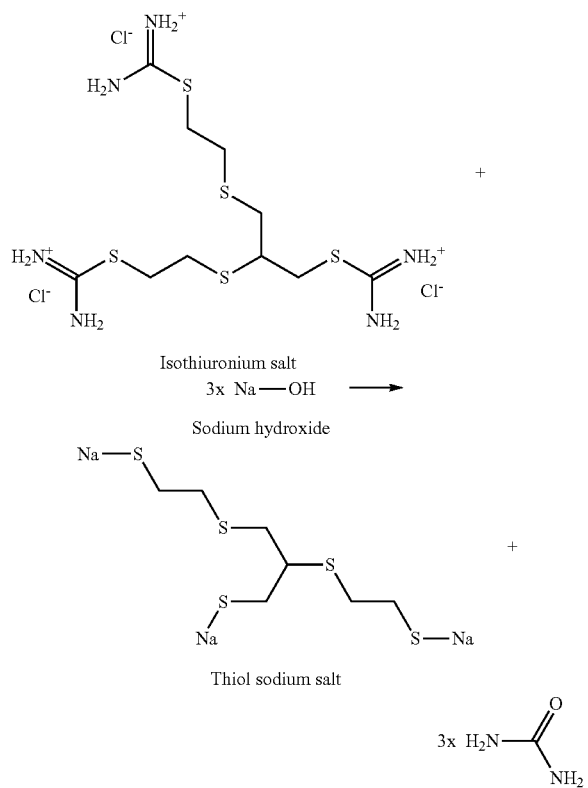

Isothiuronium salt
3x Na—OH ⟶
Sodium hydroxide

Thiol sodium salt

3x H₂N—C(=O)—NH₂

In the Reaction Scheme Example 8, an example is shown in which sodium hydroxide is used as the base. However, the base used in Step 3B is not limited to sodium hydroxide, and various inorganic bases and organic bases can be used. The base may be an inorganic base. Examples of the inorganic base include sodium hydroxide, potassium hydroxide, ammonia and the like. The form of base addition is not limited, but it is possible to add the base as an aqueous solution. By adding the base as an aqueous solution, it is possible to hydrolyze the isothiuronium salt with water contained in the aqueous solution in the presence of the base. The base concentration in the aqueous solution is not particularly limited, and can be, for example, about 10% by mass to 60% by mass. The base can be used at a ratio of, for example, 1.0 mol to 4.0 mol, 1.0 mol to 3.0 mol, or 1.2 mol to 2.0 mol with respect to 1.0 mol of the acid used in Step 2B. In Step 3B, the reaction temperature can be, for example, about 10° C. to 80° C., and the reaction time can be, for example, about 1 h to 10 h.

(Step 4B)

Step 4B is a step of converting the polythiol salt obtained in Step 3B into a polythiol with an acid. As a result, it is possible to obtain the polythiol compound represented by Formula (7). For example, Reaction Scheme Example 9 for converting the polythiol sodium salt shown in Reaction Scheme Example 8 to polythiol by using hydrogen chloride (HCl) as an acid to obtain the polythiol compound represented by Formula (7) is shown below.

Reaction Scheme Example 9

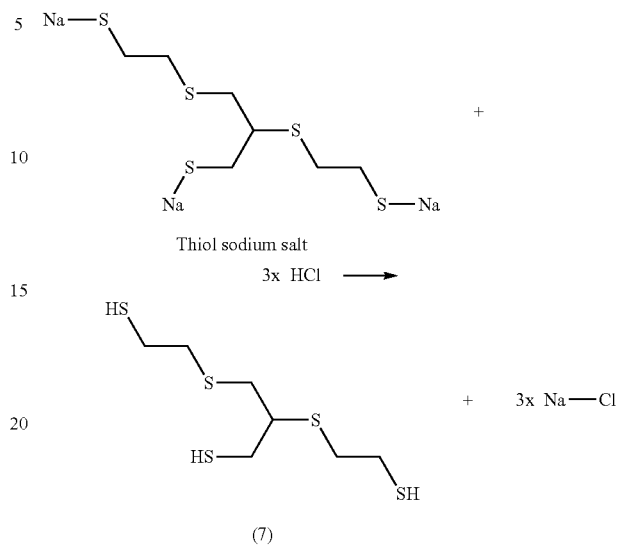

Thiol sodium salt
3x HCl ⟶

(7)

+ 3x Na—Cl

In the Reaction Scheme Example 9, an example is shown in which hydrogen chloride is used as the acid. However, the acid to be used in Step 4B is not limited to hydrogen chloride, and various inorganic acids and organic acids can be used. The details relating to the acid to be used in Step 4B are as described in relation to the acid in Step 2B. The conversion to polythiol with the acid in Step 4B may be carried out by adding the acid to the organic layer obtained by solvent extraction after Step 3B. The solvent extraction can be carried out by a known method. The conversion to polythiol with the acid may be performed using the acid as an aqueous solution, for example, by acid washing. It is possible to carry out water washing after acid washing, for example, to carry out acid washing two or more times and to wash with water between acid washing cycles. The temperature of the environment in which Step 4B is performed is not particularly limited. Step 4B can be performed in an environment with a temperature of, for example, of 10° C. to 60° C., or 20° C. to 45° C. When an organic solvent is used in any of the steps, a step of distilling off the organic solvent from the reaction solution after Step 4B may be carried out by a known method. Other steps such as filtration and distillation can also be carried out by known methods.

By the process described above, a polythiol compound represented by Formula (7) can be obtained.

Each of the polythiol compounds represented by Formula (3), (4), (5), or (7) and obtained by the method for producing a polythiol compound according to one aspect of the present disclosure is a polyfunctional polythiol compound having 3 or 4 thiol groups in a molecule. A cured product (polythiourethane resin) obtained by the curing reaction of such a polyfunctional polythiol compound with a polyiso(thio) cyanate compound can have various physical properties preferable for an optical component such as a spectacle lens.

Furthermore, according to another aspect of the present disclosure, a polythiol compound obtained by the above-mentioned production method is also provided. Regarding the physical properties of the polythiol compound, for example, the degree of coloring can be evaluated by a b* value prescribed in JIS Z8781-4:2013. It is indicated that the smaller the b* value, the less coloration is demonstrated.

With the method for producing a polythiol compound according to one aspect of the present disclosure, in one aspect, a polythiol compound having, for example, a b* value of 1.5 or less (for example, 0.5 to 1.5) can be obtained.

[Method for Producing Curable Composition]

One aspect of the present disclosure relates to a method for producing a curable composition, including:

producing a polythiol compound by the method for producing a polythiol compound according to the abovementioned one aspect of the present disclosure; and preparing a curable composition by mixing the produced polythiol compound with a polyiso(thio)cyanate compound.

Furthermore, according to still another aspect of the present disclosure, a curable composition that is obtained by the production method is also provided.

By curing the curable composition obtained by the production method, a polythiourethane resin useful as a material for an optical component such as a spectacle lens can be obtained as a cured product.

Hereinafter, the production method of the curable composition will be described in greater detail.

Details of the step of producing a polythiol compound are as described above in relation to the method for producing a polythiol compound according to one aspect of the present disclosure. A curable composition can be prepared by mixing the thus produced polythiol compound with a polyiso(thio)cyanate compound. In the present disclosure and in the present description, the term "polyiso(thio)cyanate compound" is intended to be inclusive of a polyisocyanate compound and a polyisothiocyanate compound. Incidentally, isocyanate can be represented by "isocyanato", and isothiocyanate can be represented by "isothiocyanato". In addition, the term "iso(thio)cyanate group" is intended to be inclusive of an isocyanate group (—N=C=O) and an isothiocyanate group (—N=C=S). A "polyiso(thio)cyanate compound" is a polyfunctional compound having two or more iso(thio)cyanate groups in a molecule. As a result of reactive curing of a polythiol compound with a polyiso(thio)cyanate compound, the thiol group of the polythiol compound reacts with the iso(thio)cyanate group of the polyiso(thio)cyanate compound, and a reaction product having the following bond:

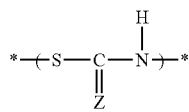

in a molecule can be obtained. In this formula, Z is an oxygen atom or a sulfur atom. As a result of reacting the thiol group with the isocyanate group, X forms the abovementioned bond with the oxygen atom, and as a result of reacting with the isothiocyanate group, X forms the abovementioned bond with the sulfur atom. In the present disclosure and the present description, a reaction product (resin) having a plurality of the abovementioned bonds in a molecule is described as "polythiourethane resin".

As the polyiso(thio)cyanate compound, various polyiso(thio)cyanate compounds such as aliphatic polyiso(thio)cyanate compounds, alicyclic polyiso(thio)cyanate compounds and aromatic polyiso(thio)cyanate compounds can be used. The number of iso(thio)cyanate groups contained in one molecule of the polyiso(thio)cyanate compound is 2 or more, may be 2 to 4, and may be 2 or 3. Specific examples of polyiso(thio)cyanate compounds include various compounds exemplified as polyiso(thio)cyanate compounds, for example, in paragraph 0052 of Japanese Patent No. 5319037 (the entire disclosure of which is hereby specifically incorporated by reference). Examples of polyiso(thio)cyanate compounds include aliphatic polyisocyanate compounds such as hexamethylene diisocyanate, 1,5-pentane diisocyanate, isophorone diisocyanate, bis(isocyanatomethyl)cyclohexane, dicyclohexylmethane diisocyanate, 2,5-bis(isocyanatomethyl)-bicyclo[2.2.1]heptane, 2,6-bis(isocyanatomethyl)-bicyclo[2.2.1]heptane, bis(4-isocyanatocyclohexyl)methane, 1,3-bis(isocyanatomethyl)cyclohexane and 1,4-bis(isocyanatomethyl)cyclohexane, and aromatic polyisocyanate compounds such as xylylene diisocyanate, 1,3-diisocyanatobenzene, tolylene diisocyanate, 2,4-diisocyanatotoluene, 2,6-disocyanatotoluene and 4,4'-methylenebis(phenylisocyanate). Further, halogen substituents such as chlorine substituents and bromine substituents, alkyl substituents, alkoxy substituents, nitro substituents, prepolymer modification products with polyhydric alcohols, carbodiimide modification products, urea modification products, biuret modification products, dimer modification products, and trimer modification products of the polyiso(thio)cyanate compound can be also used. These compounds may be used singly or in combination of two or more thereof.

The curable composition can be prepared by mixing the polythiol compound with a polyiso(thio)cyanate compound. The mixing ratio of the polythiol compound and the polyiso(thio)cyanate compound in the curable composition is not particularly limited and can be, for example, in the range of 0.5 to 3.0, in the range of 0.6 to 2.0, or in the range of 0.8 to 1.3, as a molar ratio of thiol groups contained in the polythiol compound to iso(thio)cyanate groups contained in the polyiso(thio)cyanate compound. Setting the mixing ratio within the above ranges is possible in terms of obtaining a curable composition capable of providing a cured product having various excellent physical properties such as high refractive index and high heat resistance. Further, in one aspect, the curable composition can include, for example, 40% by mass or more (for example, 40% by mass to 70% by mass) of the polythiol compound with respect to 100% by mass of the total amount of the curable composition.

At the time of preparing the curable composition, one or more components other than the polythiol compound and the polyiso(thio)cyanate compound may be mixed. Specific examples of such other components include, for example, a reaction catalyst for the curing reaction between the polythiol compound and the polyiso(thio)cyanate compound. For other components that may be mixed, see, for example, Japanese Patent No. 5319037, paragraphs 0055, 0057, and 0058 to 0064. In addition, it is also possible to use one or more additives commercially available as additives for various resins such as polythiourethane resins. The curable composition can be prepared by mixing the above-described various components at the same time or sequentially in any order. The preparation method is not particularly limited, and any known method for preparing curable compositions can be used without any limitation.

[Method for Producing Cured Product]

According to one aspect of the present disclosure, there is provided a method for producing a cured product, including:

producing a curable composition by the production method according to the abovementioned one aspect of the present disclosure; and curing the produced curable composition to obtain a cured product.

According to yet another aspect of the present disclosure, there is also provided a cured product obtained by the abovementioned production method.

Hereinafter, the method for producing a cured product will be described in greater detail.

Details relating to the step of producing the curable composition are as described above in relation to the method for producing the curable composition according to one aspect of the present disclosure. By curing the curable composition thus produced, it is possible to obtain a polythiourethane resin useful as a material for an optical component such as a spectacle lens as a cured product. As a result of intensive investigation conducted by the inventors of the present disclosure, it has been found that by using the polythiol compound obtained by the method for producing a polythiol compound according to one aspect of the present disclosure as a raw material for synthesis, the tensile strength of the obtained polythiourethane can be improved without causing a significant decrease in heat resistance. Regarding the tensile strength, it is possible that the tensile strength measured in the below-described Examples could be improved by 1 kgf/cm$^2$ or more, for example, 2 kgf/cm$^2$ or more (for example, 2 kgf/cm$^2$ to 8 kgf/cm$^2$). Meanwhile, an indicator of heat resistance can be exemplified by a glass transition temperature (Tg). The glass transition temperature (Tg) in the present disclosure and the present description refers to a glass transition temperature measured by thermomechanical analysis (TMA) penetration method according to JIS K7196-2012. For a specific measurement method, refer to the below-described Examples. Regarding the heat resistance with the glass transition temperature (Tg) as an index, it is possible that the decrease in heat resistance be 2° C. or less as Tg.

The curing reaction between the polythiol compound and the polyiso(thio)cyanate compound can be carried out by various types of curing treatment capable of curing the curable composition. For example, cast polymerization is possible for producing a cured product having a lens shape (also referred to as "plastic lens"). In cast polymerization, a cured product can be obtained by injecting a curable composition into a cavity of a molding die having two opposed molds with a predetermined gap therebetween and a cavity formed by closing the gap, and polymerizing (curing) the curable composition inside the cavity. For details of molds that can be used for cast polymerization, see paragraphs 0012 to 0014 of Japanese Patent Application Laid-open No. 2009-262480 (the entire disclosure of which is hereby specifically incorporated by reference) and FIG. 1 of the same publication. In this publication, a molding die in which the gap between the two molds is closed with a gasket as a sealing member is shown, but a tape can also be used as the sealing member.

In one aspect, cast polymerization can be carried out in the following manner. The curable composition is poured into a molding die cavity from an injection port provided on the side of the molding die. After the injection, the curable composition may be polymerized (curing reaction) by heating, whereby the curable composition is cured to obtain a cured product onto which the inner shape of the cavity has been transferred. The polymerization conditions are not particularly limited, and can be appropriately set according to the composition of the curable composition or the like. As an example, the molding die with the curable composition injected into the cavity can be heated at a heating temperature of 20° C. to 150° C. for about 1 h to 72 h, but this condition is not limiting. In the present disclosure and present description, the temperature such as the heating temperature and the like relating to cast polymerization is the temperature of the atmosphere in which the molding die is disposed. In addition, it is possible to raise the temperature at an arbitrary heating rate during heating, and to lower the temperature (cool down) at an arbitrary temperature lowering rate. After completion of the polymerization (curing reaction), the cured product inside the cavity is released from the molding die. The cured product can be released from the molding die by removing the upper and lower molds forming the cavity and the gasket or tape in an arbitrary order, as is usually done in cast polymerization. The cured product released from the mold can be used as a lens base material for spectacle lenses. The cured product to be used as the lens base material for spectacle lenses usually can be subjected to post-processing after the release from the molding die, for example, annealing, a grinding step such as a rounding step, a polishing step, and a coat layer forming step of forming a primer coat layer for improving impact resistance, a hard coat layer for improving the surface hardness, and the like. Further, various functional layers such as an antireflection layer and a water-repellent layer can be formed on the lens base material. For any of these steps, known techniques can be used without any limitation. Thus, a spectacle lens in which the lens base material is the cured product can be obtained. Further, by attaching this spectacle lens to the frame, glasses can be obtained. A high tensile strength is possible for the lens base material from the viewpoint of suppressing the occurrence of fissures and cracks when attaching the spectacle lens to the frame. Further, a high tensile strength is also possible for the lens base material from the viewpoint of suppressing the occurrence of fissures and cracks which can be caused by the application of a strong force to the spectacle lens when the user is wearing spectacles equipped with spectacle lenses. In view of the above, the cured product (polythiourethane resin) obtained by the method for producing a cured product according to one aspect of the present disclosure is advantageous as a lens base material for a spectacle lens.

EXAMPLES

Next, the present disclosure will be described in greater detail with reference to Examples, but the present disclosure is not limited to the aspects shown in the Examples. Operations and evaluations described below were carried out in air at room temperature (about 20° C. to 25° C.) unless otherwise specified. In addition, "%" and "parts" described below are based on mass unless otherwise specified.

Example 1

<Production of Polythiol Compound>

(Step 1A)

A total of 0.74 g of 2,3-dichloro-1-propanol was added to epichlorohydrin to prepare 92.5 g of a mixture of the epichlorohydrin and 2,3-dichloro-1-propanol.

A total of 92.5 g (1.00 mol) of the prepared mixture was dropwise added over 1 h to a mixed solution of 78.1 g (1.00 mol) of 2-mercaptoethanol and 2.0 g of triethylamine while keeping the internal temperature at 35° C. to 40° C., and the mixture was aged over 1 h at an internal temperature of 40° C. The aging here and the aging described below were carried out while stirring the reaction solution.

(Step 2A)

An aqueous solution prepared by dissolving 125.0 g (0.50 mol) of sodium sulfide nonahydrate in 100 g of pure water was added dropwise over 1 h to the reaction solution after the aging while keeping the internal temperature at 40° C. to 45° C., followed by aging for 1 h at 45° C.

(Step 3A)

Next, 303.8 g (3.00 mol) of 36% hydrochloric acid and 190.3 g (2.5 mol) of thiourea were added to the reaction solution, and the mixture was refluxed for 9 h at an internal temperature of 110° C.

(Step 4A)

After cooling the reaction solution to room temperature, 400 ml of toluene was added, 600.4 g (4.50 mol) of a 30% sodium hydroxide aqueous solution was gradually added and hydrolysis was carried for 4 h out at an internal temperature of 60° C.

(Step 5A)

The reaction solution after the hydrolysis was allowed to stand to separate the solution into an aqueous layer and an organic layer, the organic layer was then taken out, and the organic layer was successively washed twice with 100 ml of 36% hydrochloric acid and 100 ml of water. Toluene in the organic layer after washing was distilled off with a rotary evaporator to obtain a polythiol compound in a yield of 166.1 g (yield ratio 90.6%).

In Example 1, in Step 3A, the rearrangement reaction occurs as described above, whereby a mixture of the isothiuronium salt having the skeleton of the polythiol compound represented by Formula (3), the isothiuronium salt having the skeleton of the polythiol compound represented by Formula (4), and the isothiuronium salt having the skeleton of the polythiol compound represented by Formula (5) can be obtained. As a result, in Step 5A, a mixture of the polythiol compound represented by Formula (3), the polythiol compound represented by Formula (4), and the polythiol compound represented by Formula (5) is obtained. The yield ratio was calculated by the formula Yield Ratio=[(the abovementioned yield)/(theoretical yield)]×100 by using the theoretical yield determined from the theoretical molar yield (0.5 mol) of the polythiol compounds represented by Formulas (3) to (5) obtained from the amount of 2-mercaptoethanol (1.0 mol) used in Step 1A.

Mixtures of the polythiol compound represented by Formula (3), the polythiol compound represented by Formula (4), and the polythiol compound represented by Formula (5) are similarly obtained in Examples 2 to 11 and Comparative Examples 1 to 3 described hereinbelow.

The polythiol compounds obtained in the Examples and Comparative Examples were used as they were, without treatment such as purification, for the production of the following cured products and the evaluation of polythiol compounds. The same is also true with respect to Examples and Comparative Examples described hereinbelow.

<Production of Cured Product (Plastic Lens)>

A total of 50.60 parts of xylylene diisocyanate, 0.01 parts of dimethyltin dichloride as a curing catalyst, 0.20 parts of an acidic phosphoric acid ester (JP-506H, manufactured by Johoku Chemical Co., Ltd.) as a releasing agent, and 0.50 parts of an ultraviolet absorber (SEESORB 701, manufactured by Shipro Kasei Kaisha, Ltd.) were mixed and dissolved.

Further, 49.40 parts of the polythiol compound obtained above was added and mixed to obtain a mixed solution. This mixed solution was deaerated for 1 h at 200 Pa, and then filtration was carried out with a PTFE (polytetrafluoroethylene) filter having a pore size of 5.0 μm. The filtered mixed solution (curable composition) was injected into a molding die for a lens made of a glass mold having a diameter of 75 mm and −4.00 D or 0.00 D and a tape. The molding die was loaded into an electric furnace, gradually heated over 20 h from 15° C. to 120° C., and kept for 2 h for polymerization (curing reaction). After completion of the polymerization, the molding die was removed from the electric furnace and the polymer was released to obtain a cured product (plastic lens). The resulting plastic lens was further annealed for 3 h in an annealing furnace having a furnace temperature of 120° C.

Examples 2 to 7, 10 and 11, Comparative Examples 1 and 2

In Examples 2 to 7, 10 and 11, and Comparative Example 2, the polythiol compounds were produced and the cured products were produced in the same manner as in Example 1 except that halides shown in Table 1 were used as the halide to be selected from the group consisting of a 2,3-dihalogeno-1-propanol and an allyl halide, and these halides were mixed with an epichlorohydrin so that the amount of the halide had a value shown in Table 1 with respect to the total amount with the epichlorohydrin.

In Comparative Example 1, the polythiol compound was produced and the cured product was produced in the same manner as in Example 1 except that the halide selected from the group consisting of a 2,3-dihalogeno-1-propanol and an allyl halide was not mixed with an epichlorohydrin.

Examples 8 and 9, Comparative Example 3

In Examples 8 and 9, the polythiol compounds were produced in the same manner as in Example 1 except that the halide shown in Table 1 was used as the halide to be selected from the group consisting of a 2,3-dihalogeno-1-propanol and an allyl halide, and the halide was mixed with an epichlorohydrin so that the amount of the halide had a value shown in Table 1 with respect to the total amount with the epichlorohydrin.

In Examples 8 and 9, cured products (plastic lenses) were produced by the following method using the polythiol compound thus produced. In Comparative Example 3, a cured product (plastic lens) was produced by the following method by using the polythiol compound produced by the same method as in Comparative Example 1.

A total of 58.90 parts of dicyclohexylmethane diisocyanate, 0.30 parts of dimethyltin dichloride as a curing catalyst, 0.20 parts of an acidic phosphoric acid ester (JP-506H manufactured by Johoku Chemical Co., Ltd.) as a releasing agent, and 0.50 parts of an ultraviolet absorber (SEESORB 701, manufactured by Shipro Kasei Kaisha, Ltd.) were mixed and dissolved.

Further, 41.10 parts of the polythiol compound obtained by the production of the polythiol compound was added and mixed to obtain a mixed solution. This mixed solution was deaerated for 1 h at 200 Pa, and then filtration was carried out with a PTFE (polytetrafluoroethylene) filter having a pore size of 5.0 μm. The filtered mixed solution (curable composition) was injected into a molding die for a lens made of a glass mold having a diameter of 75 mm and −4.00 D or 0.00 D and a tape. The molding die was loaded into an electric furnace, gradually heated over 20 h from 15° C. to 120° C., and kept for 2 h for polymerization (curing reaction). After completion of the polymerization, the molding die was removed from the electric furnace and the polymer was released to obtain a cured product (plastic lens). The resulting plastic lens was further annealed for 3 h in an annealing furnace having a furnace temperature of 120° C.

Example 12

<Production of Polythiol Compound>

(Step 1B)

A total of 0.24 g of 2,3-dichloro-1-propanol was added to an epichlorohydrin to prepare 30.0 g of a mixture of the epichlorohydrin and 2,3-dichloro-1-propanol.

A total of 30.0 g (0.32 mol) of the mixture was dropwise added over 1 h to a solution prepared by dissolving 53.2 g (0.68 mol) of 2-mercaptoethanol and 27.2 g (0.68 mol) of sodium hydroxide in 200 ml of ethanol while maintaining the internal temperature at 20° C.

After completion of the dropwise addition, the reaction solution was heated and aged for 1 h at an internal temperature of 50° C.

(Step 2B)

The solution after the aging was cooled to room temperature, 40.5 g (0.40 mol) of 36% hydrochloric acid was added, and vacuum concentration was performed.

A total of 203 g (2.00 mol) of 36% hydrochloric acid and 92.6 g (1.22 mol) of thiourea were further added to the solution after vacuum concentration, followed by refluxing for 6 h at an internal temperature of 110° C.

(Step 3B)

The obtained reaction solution was cooled to room temperature, and 195 g (2.44 mol) of a 50% sodium hydroxide aqueous solution was added while maintaining the internal temperature at 30° C. to 40° C., followed by heating and stirring for 1 h at an internal temperature of 60° C.

(Step 4B)

After cooling the obtained solution to room temperature, an organic layer obtained was taken out by extraction with 100 ml of toluene. The organic layer was sequentially washed twice with 100 ml of 36% hydrochloric acid and 100 ml of water. Toluene in the organic layer after washing was distilled off with a rotary evaporator to obtain a target polythiol compound in a yield of 74.8 g.

In Example 12, the polythiol compound is obtained according to Aspect B. Therefore, the obtained polythiol compound is a polythiol compound represented by Formula (7).

<Production of Cured Product (Plastic Lens)>

A total of 52.00 parts of xylylene diisocyanate, 0.01 parts of dimethyltin dichloride as a curing catalyst, 0.20 parts of an acidic phosphoric acid ester (JP-506H, manufactured by Johoku Chemical Co., Ltd.) as a releasing agent, and 0.50 parts of an ultraviolet absorber (SEESORB 701, manufactured by Shipro Kasei Kaisha, Ltd.) were mixed and dissolved.

Further, 48.00 parts of the polythiol compound obtained above was added and mixed to obtain a mixed solution. This mixed solution was deaerated for 1 h at 200 Pa, and then filtration was carried out with a PTFE (polytetrafluoroethylene) filter having a pore size of 5.0 μm. The filtered mixed solution (curable composition) was injected into a molding die for a lens made of a glass mold having a diameter of 75 mm and −4.00 D or 0.00 D and a tape. The molding die was loaded into an electric furnace, gradually heated over 20 h from 15° C. to 120° C., and kept for 2 h for polymerization (curing reaction). After completion of the polymerization, the molding die was removed from the electric furnace and the polymer was released to obtain a cured product (plastic lens). The resulting plastic lens was further annealed for 3 h in an annealing furnace having a furnace temperature of 120° C.

Example 13, Comparative Example 4

In Example 13, the polythiol compound was produced and the cured product was produced in the same manner as in Example 12 except that the halide shown in Table 1 was used as the halide to be selected from the group consisting of a 2,3-dihalogeno-1-propanol and an allyl halide, and this halide was mixed with an epichlorohydrin so that the amount of the halide had a value shown in Table 1 with respect to the total amount with the epichlorohydrin.

In Comparative Example 4, the polythiol compound was produced and the cured product was produced in the same manner as in Example 12 except that the halide selected from the group consisting of a 2,3-dihalogeno-1-propanol and an allyl halide was not mixed with an epichlorohydrin.

Epichlorohydrin used in Examples and Comparative Examples had a purity of 99.5% by mass. It was confirmed by gas chromatography that this epichlorohydrin did not contain a halide selected from the group consisting of a 2,3-dihalogeno-1-propanol and an allyl halide as an impurity.

The amount of the halide selected from the group consisting of a 2,3-dihalogeno-1-propanol and an allyl halide, which is shown in Table 1, is a value calculated from the amount used and purity of the halide and epichlorohydrin used.

[Evaluation Method]

<Glass Transition Temperature (Heat Resistance)>

As an index of heat resistance, the glass transition temperature (Tg) of the plastic lenses obtained in Examples and Comparative Examples was measured by a penetration method using a thermal instrument analyzer TMA 8310 manufactured by Rigaku Corporation. The load at the time of measurement was 10 g, the heating rate was 10 K/min, and an indenter with a diameter of 0.5 mm was used as an indenter for the penetration method.

<Tensile Strength>

The plastic lens (0.00 D) obtained in Examples and Comparative Examples was rounded to a diameter of 50.0 mm to prepare a sample lens for tensile strength measurement.

A hole having a diameter of 1.6 mm was opened at two positions facing each other across the center at 21.0 mm from the center of each sample lens, and two holes were formed in each sample lens.

A fixing pin of the tensile testing machine was attached to each hole of the sample, the sample lens was set in the tensile tester, and the tensile strength was measured (pulling rate: 5.0 mm/min). A universal testing machine RTC-1225A manufactured by Orientec Co., Ltd. was used as the tensile testing machine.

<Coloration (b* Value) of Polythiol Compound>

The b* values of the polythiol compounds obtained in Examples and Comparative Examples were measured with an optical path length of 10 mm by using a spectrophotometer U-3500 manufactured by Hitachi, Ltd.

The above results are shown in Table 1. By the comparison between Examples 1 to 11 and Comparative Examples 1 and 2, between Examples 8 and 9 and Comparative Example 3, and between Examples 12 and 13 and Comparative Example 4 shown in Table 1, it can be confirmed that by carrying out the step of reacting 2-mercaptoethanol with an epihalohydrin in the production of a polythiol compound in the presence of a halide selected from the group consisting of a 2,3-dihalogeno-1-propanol and an allyl halide, with the amount of the halide being more than 0.50% by mass and 10.00% by mass or less with respect to the total amount of the halide and the epihalohydrin, it is possible to improve the tensile strength of the cured product produced using the obtained polythiol compound without causing a large decrease in heat resistance (large decrease in glass transition temperature).

In one aspect, one or more polythiol compounds selected from the group consisting of the polythiol compound represented by Formula (3), the polythiol compound represented by Formula (4) and the polythiol compound represented by Formula (5) are produced by the abovementioned method for producing a polythiol compound.

In one aspect, the polythiol compound represented by Formula (7) is produced by the abovementioned method for producing the polythiol compound.

TABLE 1

| | Halide | | Raw material for plastic lens | | b* value of polythiol compound | Glass transition temp. of plastic lens (° C.) | Tensile strength of plastic lens (kgf/cm²) |
|---|---|---|---|---|---|---|---|
| | Type | Halide amount related to the total amount of halide and epichlorohydrin | Polythiol compound | Polyiso-(thio)cyanate compound | | | |
| Ex. 1 | Cl | 0.80% | Formula (3) + | Xylylene | 1.1 | 102 | 67 |
| Ex. 2 | Cl | 1.20% | Formula (4) + | diisocyanate | 1.1 | 102 | 67 |
| Ex. 3 | Cl | 3.00% | Formula (5) | | 1.1 | 101 | 68 |
| Ex. 4 | Cl | 4.80% | | | 1.1 | 101 | 69 |
| Ex. 5 | Cl | 10.00% | | | 1.1 | 100 | 71 |
| Ex. 6 | Br | 4.80% | | | 1.2 | 101 | 68 |
| Ex. 7 | Br | 10.00% | | | 1.2 | 101 | 69 |
| Ex. 10 | Cl AC | 1.20% 1.20% | | | 1.1 | 102 | 67 |
| Ex. 11 | AC | 4.80% | | | 1.1 | 100 | 67 |
| Comp. Ex. 1 | — | 0.00% | | | 1.1 | 102 | 65 |
| Comp. Ex. 2 | Cl | 20.00% | | | 1.1 | 97 | 71 |
| Ex. 8 | Cl | 4.80% | Formula (3) + | Dicyclohexyl | 1.1 | 145 | 56 |
| Ex. 9 | Cl | 10.00% | Formula (4) + | methane | 1.1 | 144 | 57 |
| Comp. Ex. 3 | — | 0.00% | Formula (5) | diisocyanate | 1.1 | 146 | 54 |
| Ex. 12 | Cl | 0.80% | Formula (7) | Xylylene | 0.8 | 87 | 67 |
| Ex. 13 | Cl | 4.80% | | diisocyanate | 0.8 | 85 | 68 |
| Comp. Ex. 4 | — | 0.00% | | | 0.7 | 87 | 65 |

(In the table, Cl: 2,3-dichloro-1-propanol, Br: 2,3-dibromo-1-propanol, AC: allyl chloride)

Finally, the above-mentioned aspects are summarized.

According to one aspect, there is provided a method for producing a polythiol compound, including reacting 2-mercaptoethanol with an epihalohydrin, wherein the reaction is carried out in the presence of a halide selected from the group consisting of a 2,3-dihalogeno-1-propanol and an allyl halide, and the amount of the halide in the reaction is more than 0.50% by mass and 10.00% by mass or less with respect to the total amount of the halide and the epihalohydrin.

By the curing reaction of the polythiol compound obtained by the abovementioned method for producing a polythiol compound with a polyiso(thio)cyanate compound, it is possible to provide a cured product (polythiourethane resin) having a high tensile strength without causing a large decrease in heat resistance.

In one aspect, the halide is composed of 2,3-dichloro-1-propanol.

In one aspect, the halide is composed of 2,3-dibromo-1-propanol.

In one aspect, the halide is composed of allyl chloride.

In one aspect, the halide composed of 2,3-dichloro-1-propanol and allyl chloride.

In one aspect, the amount of the halide may be 9.00% by mass or less, may be 8.00% by mass or less, may be 7.00% by mass or less, may be 6.00% by mass or less, may be 5.00% by mass or less, and may be 4.00% by mass or less, 3.00% by mass or less, 2.00% by mass or less, and 1.50% by mass or less.

According to further aspect, there is provided a method for producing a curable composition, including: producing a polythiol compound by the abovementioned production method; and mixing the produced polythiol compound with a polyiso(thio)cyanate compound to prepare a curable composition.

According to still further aspect, there is provided a method for producing a cured product, including: producing a curable composition by the abovementioned production method; and curing the produced curable composition to obtain a cured product.

In one aspect, the curing is carried out by subjecting the curable composition to cast polymerization.

In one aspect, the cured product is a spectacle lens base material.

Two or more of the various aspects disclosed in this description can be combined in any combination.

It should be taken into account that the embodiments disclosed herein are exemplary in all respects and are not restrictive. The scope of the present disclosure is defined not by the description above but by the claims, and is intended to include all modifications within the meaning and scope equivalent to the claims.

One aspect of the present disclosure is useful in the field of manufacturing various kinds of optical components such as spectacle lenses.

What is claimed is:

1. A method for producing a polythiol compound, comprising reacting 2-mercaptoethanol with an epihalohydrin, wherein
the reaction is carried out in the presence of a halide selected from the group consisting of a 2,3-dihalogeno-1-propanol and an allyl halide, and
an amount of the halide in the reaction is 0.60% by mass or more and 10.00% by mass or less with respect to the total amount of the halide and the epihalohydrin.

2. The method for producing a polythiol compound according to claim 1, wherein one or more polythiol compounds selected from the group consisting of a polythiol compound represented by Formula (3) below, a polythiol compound represented by Formula (4) below, and a polythiol compound represented by Formula (5) below is produced.

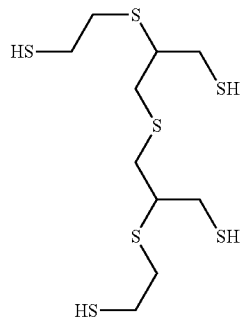

Formula (3)

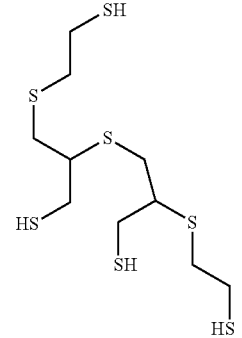

Formula (4)

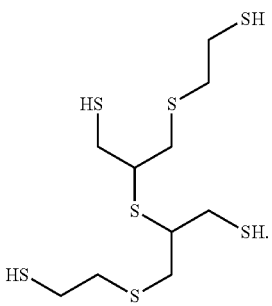

Formula (5)

3. The method for producing a polythiol compound according to claim 1, wherein a polythiol compound represented by Formula (7) below is produced.

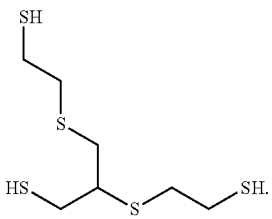

Formula (7)

4. The method for producing a polythiol compound according to claim 1, wherein an amount of the halide in the reaction is 0.70% by mass or more and 10.00% by mass or less with respect to the total amount of the halide and the epihalohydrin.

5. The method for producing a polythiol compound according to claim 1, wherein an amount of the halide in the reaction is 0.80% by mass or more and 10.00% by mass or less with respect to the total amount of the halide and the epihalohydrin.

* * * * *